United States Patent
Desnerck et al.

(10) Patent No.: US 10,964,422 B2
(45) Date of Patent: Mar. 30, 2021

(54) APPARATUS AND METHOD FOR USER EXERCISE MONITORING

(71) Applicant: BIOMET GLOBAL SUPPLY CHAIN CENTER B.V., Dordrecht (NL)

(72) Inventors: Simon Philippe Paul Maria Desnerck, Kalken (BE); Samy Andary, Delft (NL); Alec Momont, Vossom (BE); Mathijs Rien De Schipper, Delft (NL); Mick Winters, The Hague (NL); Kiki Kraak, Delft (NL); Andriy Yasynetskyy, Delft (NL)

(73) Assignee: Biomet Global Supply Chain Center, B.V., Dordrecht (NL)

( * ) Notice: Subject to any disclaimer, the term of this patent is extended or adjusted under 35 U.S.C. 154(b) by 224 days.

(21) Appl. No.: 15/021,480

(22) PCT Filed: Sep. 12, 2014

(86) PCT No.: PCT/EP2014/069571
§ 371 (c)(1),
(2) Date: Mar. 11, 2016

(87) PCT Pub. No.: WO2015/039979
PCT Pub. Date: Mar. 26, 2015

(65) Prior Publication Data
US 2016/0220176 A1    Aug. 4, 2016

(30) Foreign Application Priority Data

Sep. 18, 2013 (GB) ...................................... 1316566

(51) Int. Cl.
*G16H 20/30* (2018.01)
*A61B 5/00* (2006.01)
(Continued)

(52) U.S. Cl.
CPC ............ *G16H 20/30* (2018.01); *A61B 5/1118* (2013.01); *A61B 5/1123* (2013.01); *A61B 5/486* (2013.01);
(Continued)

(58) Field of Classification Search
CPC ..... A61B 5/486; A61B 5/6831; A61B 5/7246; A61B 5/742; A61B 5/1123; A61B 5/681;
(Continued)

(56) References Cited

U.S. PATENT DOCUMENTS 6,556,222 B1 * 4/2003 Narayanaswami .. G04G 9/0064
                                                     368/295
6,686,911 B1 * 2/2004 Levin ..................... G05G 9/047
                                                     345/156

(Continued)

FOREIGN PATENT DOCUMENTS

CN      103154954     6/2013
CN      103210355     7/2013
(Continued)

OTHER PUBLICATIONS

IEEE 100. [Electronic Resource] : The Authoritative Dictionary of IEEE Standards Terms. New York : Standards Information Network, IEEE Press, 2000., 2000. EBSCOhost.*
(Continued)

*Primary Examiner* — Sean P Dougherty
(74) *Attorney, Agent, or Firm* — Schwegman Lundberg & Woessner, P.A.

(57) ABSTRACT

An apparatus (2) for user exercise monitoring is disclosed. The apparatus (2) comprises a frame (4), a motion sensing unit (10) and a user input unit (12) supported by the frame (4), and a harness (6) configured to secure the frame (4) to a user body part. The user input unit (12) comprises a continuous input device (72). Also disclosed is a method for
(Continued)

monitoring user exercise via a monitoring apparatus (2) secured to the user. The method comprises sensing user motion with the monitoring apparatus (2) and receiving, via the motioning apparatus (2), user input during exercise. The user input is received via a continuous input device (72) on the monitoring apparatus.

17 Claims, 8 Drawing Sheets

(51) Int. Cl.
*A61B 5/11* (2006.01)
*G06F 3/0362* (2013.01)
*G06F 1/16* (2006.01)

(52) U.S. Cl.
CPC ............ *A61B 5/4824* (2013.01); *A61B 5/681* (2013.01); *A61B 5/6831* (2013.01); *A61B 5/7246* (2013.01); *A61B 5/742* (2013.01); *A61B 5/7475* (2013.01); *G06F 1/163* (2013.01); *G06F 3/0362* (2013.01); *A61B 2560/0475* (2013.01); *A61B 2560/0487* (2013.01); *A61B 2562/0219* (2013.01)

(58) Field of Classification Search
CPC ... A61B 5/4824; A61B 5/1118; A61B 5/7475; A61B 2562/0219; A61B 2560/0475; A61B 2560/0487; G06F 19/3481; G06F 1/163; G06F 3/0362
See application file for complete search history.

(56) References Cited

U.S. PATENT DOCUMENTS

| | | | |
|---|---|---|---|
| 7,510,508 B2 * | 3/2009 | Santomassimo | A63B 24/00 482/1 |
| 8,812,419 B1 * | 8/2014 | Teller | G06Q 10/10 706/46 |
| 2003/0103032 A1 | 6/2003 | Wong et al. | |
| 2004/0267099 A1 * | 12/2004 | McMahon | A61B 5/00 600/300 |
| 2005/0172311 A1 * | 8/2005 | Hjelt | A61B 5/1112 725/10 |
| 2005/0209051 A1 | 9/2005 | Santomassimo et al. | |
| 2006/0122521 A1 | 6/2006 | Chen | |
| 2006/0264299 A1 * | 11/2006 | Farinelli | A63B 23/0211 482/8 |
| 2007/0035403 A1 * | 2/2007 | Krishna | G16H 40/67 340/573.1 |
| 2008/0096726 A1 * | 4/2008 | Riley | A63B 24/0075 482/8 |
| 2009/0054751 A1 | 2/2009 | Babashan et al. | |
| 2009/0069642 A1 * | 3/2009 | Gao | A61B 5/02055 600/300 |
| 2009/0190713 A1 | 7/2009 | Wai | |
| 2010/0156653 A1 * | 6/2010 | Chaudhari | G01C 9/00 340/686.1 |
| 2011/0224498 A1 | 9/2011 | Banet et al. | |
| 2012/0046540 A1 * | 2/2012 | Branch | A61B 5/1036 600/415 |
| 2012/0116684 A1 * | 5/2012 | Ingrassia, Jr. | G06F 19/321 702/19 |
| 2012/0194552 A1 * | 8/2012 | Osterhout | G02B 27/0093 345/633 |
| 2012/0286953 A1 * | 11/2012 | Bousamra | G16H 50/70 340/540 |
| 2012/0289803 A1 * | 11/2012 | Weinert | G16H 20/17 600/365 |
| 2013/0085418 A1 * | 4/2013 | Salhani | A61B 5/0002 600/595 |
| 2013/0144176 A1 * | 6/2013 | Lee | A61B 5/0002 600/485 |
| 2014/0045480 A1 * | 2/2014 | Hsieh | G06F 1/1643 455/418 |
| 2014/0073486 A1 * | 3/2014 | Ahmed | A61B 5/02405 482/9 |
| 2014/0139422 A1 * | 5/2014 | Mistry | G06F 3/014 345/156 |
| 2014/0139637 A1 * | 5/2014 | Mistry | H04N 5/2252 348/46 |
| 2014/0206327 A1 * | 7/2014 | Ziemianska | A61B 5/1118 455/418 |
| 2014/0245784 A1 * | 9/2014 | Proud | A44C 5/0015 63/1.11 |

FOREIGN PATENT DOCUMENTS

| | | |
|---|---|---|
| CN | 105636516 | 6/2016 |
| JP | 2005152222 A | 6/2005 |
| JP | 2007526030 A | 9/2007 |
| JP | 2010097243 A | 4/2010 |
| JP | 2012524640 A | 10/2012 |
| JP | 2013042099 A | 2/2013 |
| JP | 2013141154 A | 7/2013 |
| JP | 2016535648 | 11/2016 |
| WO | 2012021878 | 2/2012 |
| WO | WO-2015039979 A1 | 3/2015 |

OTHER PUBLICATIONS

"European Application Serial No. 14766462.7, Response filed Nov. 14, 2016 to Communication pursuant to Rules 161(1) and 162 EPC dated May 4, 2016", 15 pgs.
"Australian Application Serial No. 2014323207, Response filed Nov. 16, 2017 to First Examination Report dated Oct. 5, 2017", 17 pgs.
"Australian Application Serial No. 2014323207, Subsequent Examiners Report dated Dec. 20, 2017", 6 pgs.
"Chinese Application Serial No. 201480057410.8, Office Action dated Nov. 16, 2017", With English Translation, 18 pgs.
"Australian Application Serial No. 2014323207, Response filed Jan. 15, 2018 to Subsequent Examiners Report dated Dec. 20, 2017", 17 pgs.
"International Application Serial No. PCT/EP2014/069571, International Preliminary Report on Patentability dated Mar. 31, 2016", 11 pgs.
"International Application Serial No. PCT/EP2014/069571, International Search Report dated Dec. 10, 2014", 6 pgs.
"International Application Serial No. PCT/EP2014/069571, Written Opinion dated Dec. 10, 2014", 9 pgs.
"Australian Application Serial No. 2014323207, First Examination Report dated Oct. 5, 2017", 4 pgs.
"Chinese Application Serial No. 201480057410.8, Office Action dated May 10, 2018", (W/ English Translation), 10 pgs.
"Chinese Application Serial No. 201480057410.8, Response filed Apr. 2, 2018 to Office Action dated Nov. 16, 2017", (W/ English Translation of Claims), 10 pgs.
"Chinese Application Serial No. 201480057410.8, Response filed Jun. 27, 2018 Office Action dated May 10, 2018", (W/ English Translation of Claims), 8 pgs.
"Japanese Application Serial No. 2016-543367, Office Action dated May 22, 2018", (W/ English Translation), 8 pgs.
"Australian Application Serial No. 2018203133, First Examination Report dated Jan. 2, 2019", 4 pgs.
"Chinese Application Serial No. 201480057410.8, Response filed Nov. 29, 2018 to Decision of Rejection dated Aug. 23, 2018", (W/ English claims), 12 pgs.
"European Application Serial No. 14766462.7, Communication Pursuant to Article 94(3) EPC dated Apr. 15, 2019", 4 pgs.
"Japanese Application Serial No. 2016-543367, Notification of Reasons for Rejection dated Jan. 15, 2019", (W/ English Translation), 9 pgs.

(56) References Cited

OTHER PUBLICATIONS

"Japanese Application Serial No. 2016-543367, Response filed Apr. 25, 2019 to Notification of Reasons for Rejection dated Jan. 15, 2019", (W/ English Claims), 11 pgs.

"Chinese Application Serial No. 201480057410.8, Decision of Rejection dated Aug. 23, 2018", W/ English Translation, 9 pgs.

"Japanese Application Serial No. 2016-543367, Response filed Aug. 22, 2018 to Office Action dated May 22, 2018", w/English Claims, 17 pgs.

"Chinese Application Serial No. 201480057410.8, Notice of Reexamination dated Jun. 25, 2019", w English translation, 16 pgs.

"Chinese Application Serial No. 201480057410.8, Response filed Jul. 18, 2019 to Notice of Reexamination dated Jun. 25, 2019", w English claims, 9 pgs.

"European Application Serial No. 14766462.7, Response filed Aug. 23, 2019 to Communication Pursuant to Article 94(3) EPC dated Apr. 15, 2019", 9 pgs.

"Chinese Application Serial No. 201480057410.8, Notice of Reexamination dated Aug. 8, 2019", w English translation, 8 pgs.

"European Application Serial No. 14766462.7, Communication Pursuant to Article 94(3) EPC dated Jan. 7, 2020", 7 pgs.

"Chinese Application Serial No. 201480057410.8, Response filed Sep. 17, 2019 to Notice of Reexamination dated Aug. 8, 2019", with English claims, 12 pages.

"Japanese Application Serial No. 2016-543367, Office Action dated Sep. 3, 2019", with English translation, 5 pages.

"Australian Application Serial No. 2018203133, Subsequent Examiners Report dated Oct. 28, 2019", 4 pages.

"Japanese Application Serial No. 2016-543367, Response filed Feb. 20, 2020 to Office Action dated Sep. 3, 2019", with English claims, 11 pages.

"European Application Serial No. 14766462.7, Response filed May 19, 2020 to Communication Pursuant to Article 94(3) EPC dated Jan. 7, 2020", 12 pages.

"European Application Serial No. 14766462.7, Summons to Attend Oral Proceedings mailed Aug. 11, 2020", 7 pgs.

\* cited by examiner

APPARATUS AND METHOD FOR USER EXERCISE MONITORING

CLAIM OF PRIORITY

This application is a U.S. National Stage Filing under 35 U.S.C. 371 from international Application No. PCT/EP2014/069571, filed on 12 Sep. 2014, and published as WO 2015/039979 Ai on 26 Mar. 2015, which claims the benefit of United Kingdom Application No. 1316566.7, filed on 18 Sep. 2013, the benefit of priority of each of which is claimed hereby, and each of which are incorporated by reference herein in its entirety.

The present invention relates to an apparatus and method for user exercise monitoring. Such monitoring may be conducted in the context of rehabilitation following an illness, injury or medical procedure.

BACKGROUND

Patients suffering from injury or recovering from medical procedures or surgical interventions typically undergo a period of recovery and rehabilitation. Joint replacement surgery is one example of a medical procedure following which a period of rehabilitation is necessary. Following initial in-patient assessment and rehabilitation treatment, a patient is typically prescribed a series of exercises in order to continue the rehabilitation process in their own home. Away from the close medical supervision provided in a hospital environment, many patients struggle with the completion of such exercise programs, failing to conduct the exercises correctly, if at all. The supervising medical practitioner, typically a physiotherapist, is reliant upon the patient for information concerning how the exercises have been performed in order to monitor and tailor the exercise program to the patient's progress. Information provided by the patient may in some cases be incomplete or inaccurate, complicating the task of the supervising practitioner. Similar difficulties may be experienced during rehabilitation following a stroke or other illnesses or medical procedures.

Personal monitoring devices are well known in the fitness industry, enabling the capture of relevant information during or after performance of certain activities. The information captured may concern a user's physical state, as in the case for example of heart rate and breathing monitors, or may relate to the activity conducted, as in motion trackers such as pedometers. Advances in sensing and communications technology have resulted in considerable expansion of this market, and in the development of a new generation of high performance activity trackers, designed to be continuously worn by a user. Activity trackers track the movement of a user and connect over wired or wireless links to a user's computer, Smartphone or other device in order to display the captured information. Such devices are primarily targeted towards the active adult population, providing insight for a user into their fitness and activity levels and acting as a motivational tool in achieving increased activity levels.

Activity trackers developed for the fitness market are generally unsuitable for the more targeted monitoring that would be useful for a rehabilitation patient. While activity trackers provide insight into general levels of activity, they are typically unable to provide information of the detail required for a medical practitioner to monitor completion of a specific exercise program. In addition, their correct operation requires certain levels of dexterity and computer literacy, as well as ownership of a compatible computing device. Joint replacement surgery, stroke illness and similar events prompting a period of rehabilitation generally affect an older population, amongst whom levels of computer literacy and Smartphone or laptop ownership are considerably lower than in the general adult population.

SUMMARY OF INVENTION

According to the present invention, there is provided an apparatus for user exercise monitoring, comprising a frame, a motion sensing unit and a user input unit supported by the frame, and a harness configured to secure the frame to a user body part. The user input unit comprises a continuous input device.

In some examples, the continuous input device may comprise a rotary device and may, for example, comprise a rotary knob and cooperating rotary displacement measurement element.

In some examples, the rotary displacement measurement element may comprise one of a potentiometer or a rotary encoder, and may for example comprise an incremental optical rotary encoder.

In some examples, the motion sensing unit may comprise at least one of an accelerometer or a gyroscope. In some examples, the motion sensing unit may comprise both an accelerometer and a gyroscope. For example, the motion sensing unit may comprise a 3-axis accelerometer and a 2-axis gyroscope.

In some examples, the user input unit may further comprise a discrete input device. The discrete input device may for example comprise a push button.

In some examples, the apparatus may further comprise a feedback unit supported by the frame. In further examples, the feedback unit may comprise a plurality of light sources. The light sources may for example comprise LEDs which may be arranged in a bank or array. The LEDs may in some examples include bi-colour LEDs.

In some examples, the feedback unit may be configured to represent input from the input unit.

In some examples, the apparatus may further comprise a memory and a processing unit, and the memory and processing unit may also be supported by the frame.

In some examples, the processing unit may be configured to receive data from the motion sensing unit and to identify completion of exercises corresponding to motion patterns stored in the memory.

In some examples, the processing unit may be further configured to store a record of completed exercises in the memory.

In some examples, the feedback unit may be further configured to display feedback from the processing unit.

According to another aspect of the present invention, there is provided a method for monitoring user exercise via a monitoring apparatus secured to the user, the method comprising sensing user motion with the monitoring apparatus and receiving, via the motioning apparatus, user input during exercise, wherein the user input is received via a continuous input device on the monitoring apparatus.

In some examples, the user input may correspond to a level of pain experienced by the user during completion of an exercise.

In some examples, the method may further comprise storing the received user input on the monitoring apparatus.

In some examples, the method may further comprise identifying within the monitoring apparatus sensed motion patterns corresponding to exercises stored in the monitoring apparatus.

In some examples, the method may further comprise providing feedback to the user via the monitoring apparatus on identifying completion of a motion pattern corresponding to a stored exercise.

In some examples, the method may further comprise storing a record of exercises completed by the user on the monitoring apparatus.

In some examples, the method may further comprise associating, in the stored record of completed exercises, received user feedback with the exercise being completed at the time of receipt of the user feedback.

In some examples, the method may further comprise comparing a sensed motion pattern to the stored motion pattern of an identified exercise and storing in the monitoring apparatus a degree of accuracy with which the exercise is completed by the user In some examples, the method may further comprise storing a program of exercises for the user on the monitoring apparatus and providing feedback via the monitoring apparatus to the user indicating the proportion of the program completed by the user.

In some examples, the method may further comprise reminding the user via the monitoring apparatus when the stored program has not been completed by the user.

BRIEF DESCRIPTION OF THE DRAWINGS

For a better understanding of the present invention, and to show more clearly how it may be carried into effect, reference will now be made, by way of example, to the following drawings, in which;—

DETAILED DESCRIPTION

Figure 1:
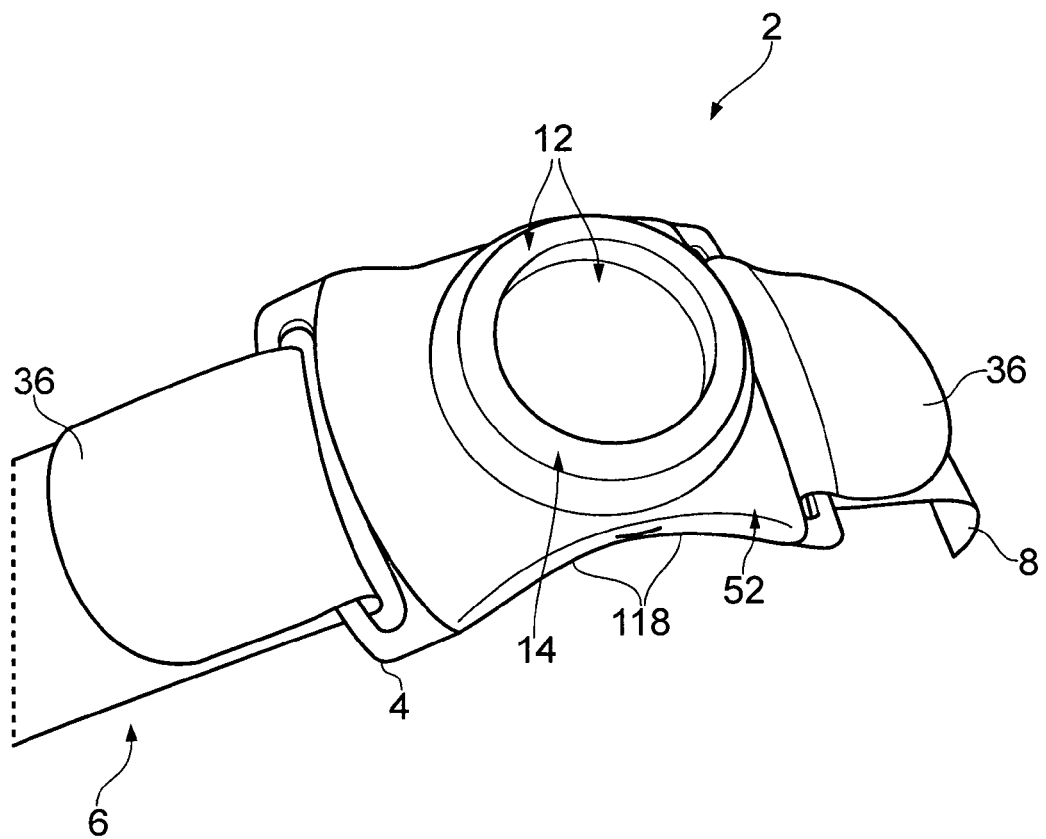
FIG. 1 is a perspective view of an apparatus for user exercise monitoring.
Figure 2:
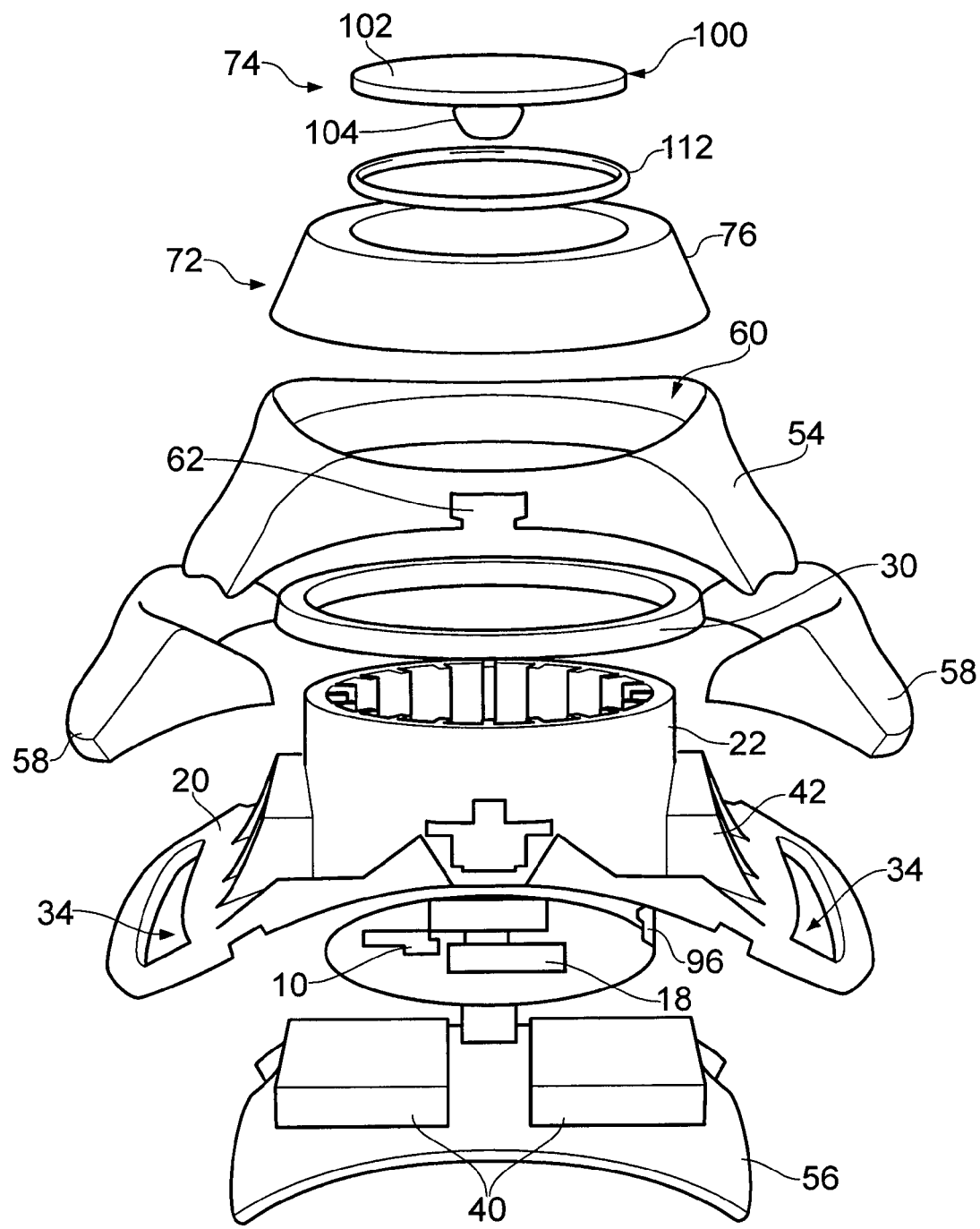
FIG. 2 is an exploded perspective view of another example of the apparatus of FIG. 1.

Referring initially to FIGS. 1 and 2, an apparatus 2 for user exercise monitoring comprises a frame 4, on which are mounted additional apparatus components. A harness 6 in the form of a strap 8 is configured to secure the frame 4 to a body part of a user, for example to a limb of a user. Mounted on the frame 4 are a motion sensing unit 10, user input unit 12 and feedback unit 14. Also mounted on the frame 4 are a processing unit 16 and a memory 18.

Referring also to FIGS. 3 to 8, the frame 4 comprises an arcuate base potion 20 with a cylindrical support 22 protruding from a central region of the base portion 20, The cylindrical support is substantially hollow, with supporting ribs 24 extending across the base of the cylindrical support 22 to define ventilation holes 26. A series of fins 28 extend radially inward from the internal circumference of the cylindrical support 22. The fins 28 are substantially evenly spaced around the inner circumference and divide the inner circumference into 20 substantially equal open segments 118, each suitable to receive an individual LED as explained in further detail below. A watertight circular bearing 30 is received over the cylindrical support 22 to rest on the base portion 20 of the frame 4 and is held in place by snap fit connectors 32 protruding from an outer circumference of the cylindrical support 22. The bearing 30 supports rotational movement of an element of the user input unit 12, as discussed in further detail below. Opposite ends of the base portion 20 of the frame 4 comprise longitudinal openings 34 extending across the width of the frame, suitable to receive opposing ends of the strap 8. In use, opposing ends 36 of the strap 8 pass through the openings 34 before folding back to be secured to the body of the strap, as described in further detail below as illustrated in FIG. 1. Velcro® or other quick release fastening may be applied to allow the ends 38 of the strap 8 to be securely attached to the main body of the strap 8 after passing through the openings 34 in the frame 4.

On a side of the frame 4 opposite to the cylindrical support 22 (a lower side as viewed in the Figures), a circuit board 38 and battery 40 are secured to the frame 4. The circuit board 38 is received immediately under the supporting ribs 24 with the battery 40 received below the circuit board 38. The battery 40 comprises two battery units, each of which is received in a housing 42 defined in the frame and held in position via a snap connection 44. Additional supporting fins 48 impart rigidity to the frame in the region between the battery housing 42 and opposing ends defining the openings 34.

Figure 3:
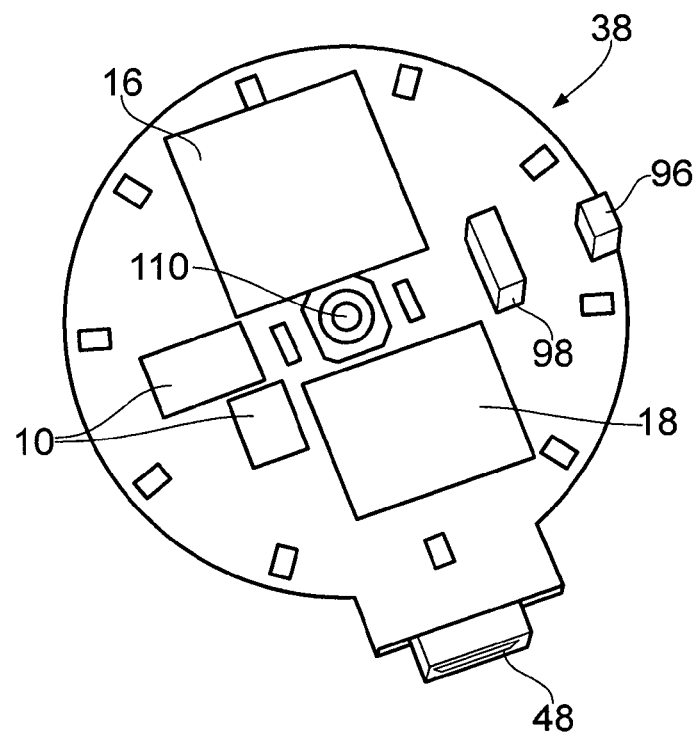
FIG. 3 is a perspective view of a circuit board of the apparatus of FIG. 1.

Referring particularly to FIG. 3, the circuit board 38 comprises a series of functional units which may be realised in a combination of hardware and/or software. In the illustrated example, many of the functional units are realised as application specific integrated circuits, as described below. A first functional unit mounted on the circuit board comprises the motion sensing unit 10. In the illustrated example, the motion sensing unit comprises a 3-axis accelerometer and a 2 axis gyroscope configured to sense linear and rotational acceleration of the apparatus 2. The accelerometer and gyroscope are mounted on the circuit board 38, and the circuit board 38 is mounted on the frame 4, such that, once the apparatus 2 is attached to a user body part, the axes of the accelerometer and gyroscope will be aligned with the principle axes of the user body. The motion sensing unit 10 is configured to send the output of the sensing elements comprised within the unit 10 to the processing unit 16. Suitable sampling rates, time intervals and measurement resolution may be selected for the measurement sensing unit 10, as discussed in further detail below.

Other functional units mounted on the circuit board 28 include the processing unit 18 and the memory 18. The processing unit 16 comprises a microprocessor and is configured to manage operation of the apparatus according to procedures outlined below with reference to FIG. 9. The memory 18 comprises a rewritable flash memory and may be sized according to the likely amount of data to be stored and the time for which data is to be retained before being downloaded to anther location. The circuit board 38 additionally supports a mini USB port 48, enabling connection via a USB cable to a computer for downloading and uploading of data onto the memory 18. An opening 50 in the frame 40 allows access to the mini USB port 48.

Figure 8:
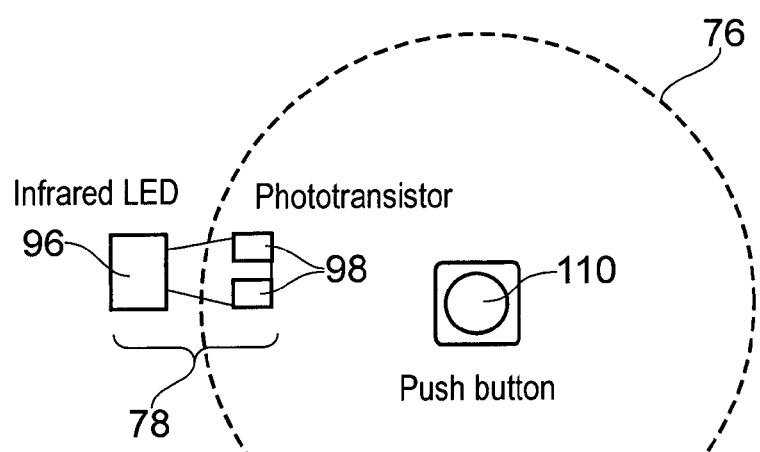
FIG. 8 is an illustration representing operation of parts of the apparatus of FIG. 1.

The frame 4, bearing 30, circuit board 38 and battery 40 are substantially encased by a housing 52 comprising an upper housing unit 54, a lower housing unit 56 and, in the example of FIG. 2, side support units 58. The upper housing unit 54 comprises a circular opening 80 and is received over the cylindrical support 22 of the frame 4, allowing the support 22 to protrude through the opening 44. The upper housing unit 54 extends away from the opening 80 to engage the frame 4. A side opening 62 in the upper housing unit 36 aligns with the opening 50 on the frame 4 to allow access to the mini USB port 48. In the example illustrated in FIG. 2, the upper housing unit 54 engages opposing ends of the frame 4 via the side support units 58. In other examples, (as shown in FIGS. 1 and 8), the upper housing unit 54 substantially directly engages the opposing ends of the frame 4 and the side support units are not present. The lower housing unit 56 engages the 40 against a lower side the frame 4. The lower housing unit 58 also provides the lower surface of the apparatus 2, and as such offers a smooth surface for engagement with a user body part. Additional rigidity may be imparted to the housing units though high density foam components 64, shaped to fit between the frame 4 and attached components and the housing units 54, 56. Connections between the housing units 54, 56 and the frame 4 may be seen in 25 FIG. 6. Upper and lower housing units are directly connected at join 68 along the sides of the apparatus 2. This connection may for example be by ultrasonic welding. The upper and lower housing units 54, 56 are connected to the frame at joins 68. The upper housing unit 54 and frame 4 are additionally connected at join 70 in the region of the bearing 30.

The user input unit 12 is mounted in the opening 60 of the upper housing unit 54, supported by the bearing 30. The user input unit 12 comprises a continuous input device 72 and a discrete input device 74. The continuous input device may comprise a linear or a rotary device, and may comprise a displaceable element and a displacement measurement element. The displacement measurement element may for example be a potentiometer or encoder.

Figure 4:
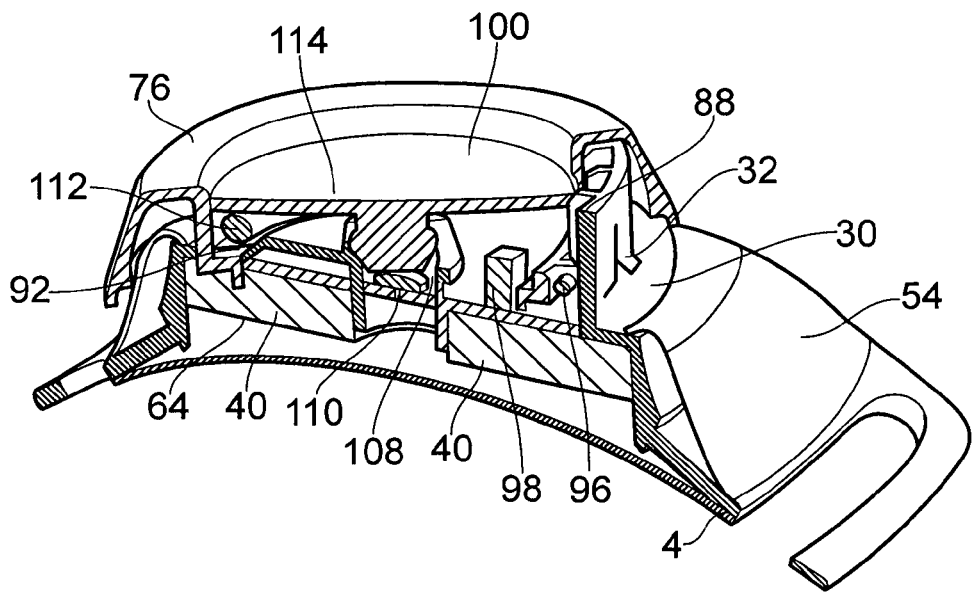
FIG. 4 is a part sectional view of the apparatus of FIG. 1.
Figure 5:
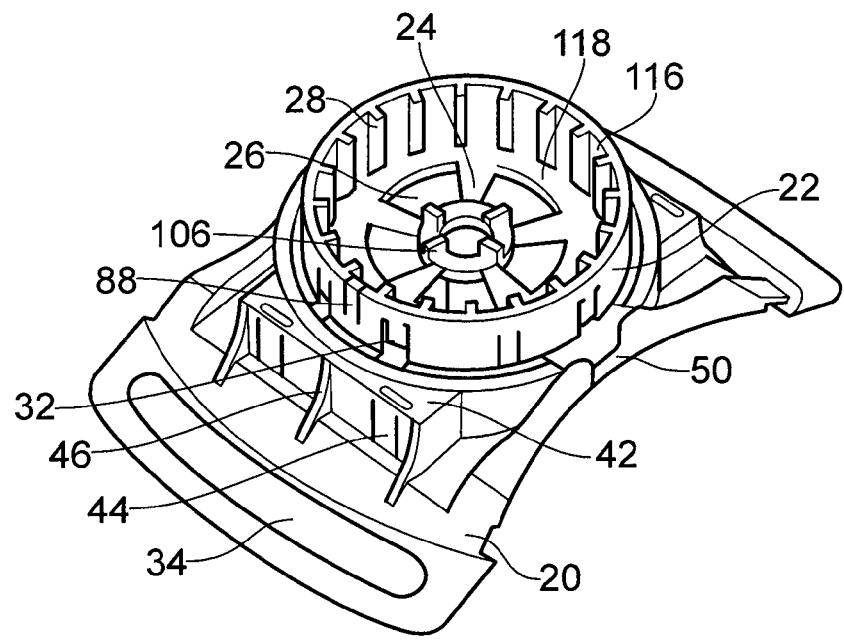
FIG. 5 is an exploded view showing connections between components of the apparatus of FIG. 1.
Figure 6:
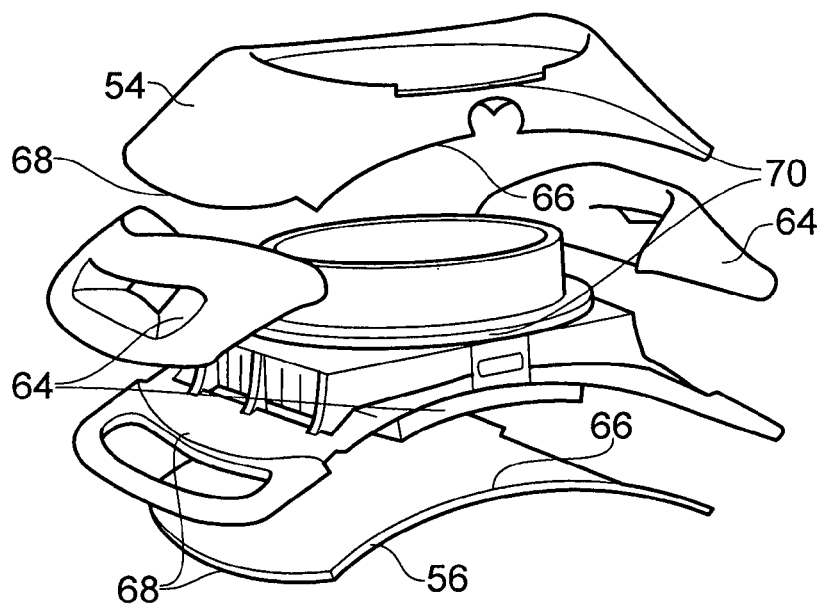
FIG. 6 is a perspective view of a frame of the apparatus of FIG. 1.
Figure 7:
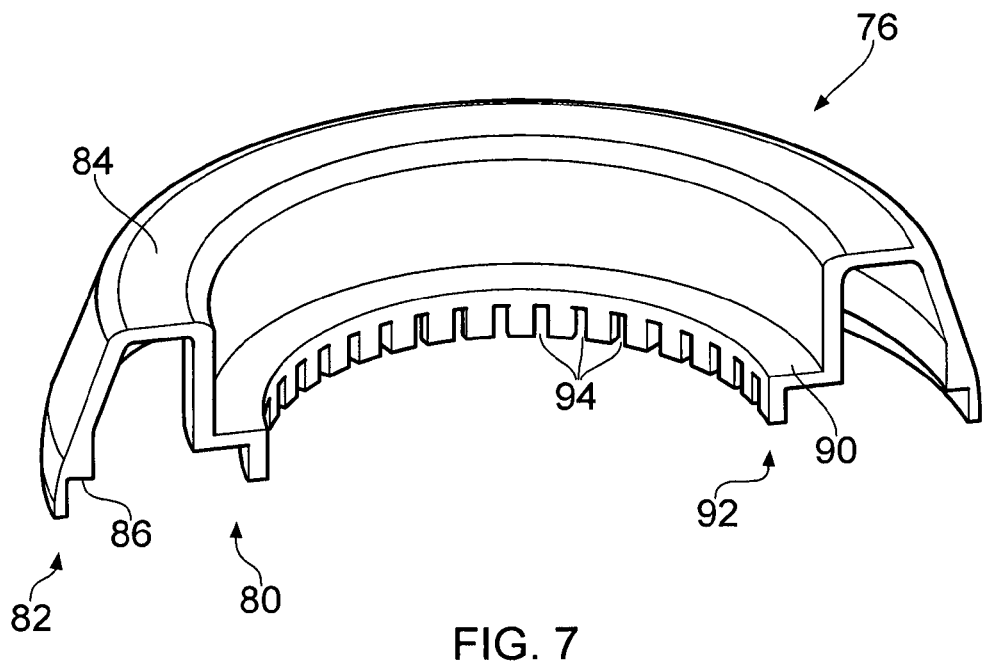
FIG. 7 is a part sectional view of a turn knob.

In the illustrated example, the continuous input device 72 is a rotary device comprising a displaceable element in the form of a turn knob 76 and a displacement measurement element in the form of an optical incremental rotary encoder 78. Referring in particular to FIGS. 4, 7 and 8, the turn knob 76 comprises an annular component having inner and outer skirts 80, 82 joined by an upper annular face 84. The cylindrical support 22 of the frame 4 is received between the inner and outer skirts 80, 82. An inner surface of the outer skirt 82 comprises an annular shoulder 86 which is slidingly received on the bearing 30. Feedback ribs 88 formed on the outer circumferential surface of the cylindrical support 22 provide mild resistance to rotation of the turn knob 78, so providing haptic feedback during rotation of the knob 76 and acting to prevent accidental rotation. The inner skirt 80 of the knob 76 comprises an inwardly extending annular shelf 90. A slotted skirt 92 extends axtally downward from an inner edge of the shelf 90. The slotted skirt 92 comprises a series of evenly spaced axial openings or slots 94 extending from a lower (as seen in the Figures) edge of the slotted skirt towards the shelf 90.

The incremental rotary encoder 78 comprises an infra red (IR) LED and a double IR sensor 98. With the turn knob 76 received in place on the bearing 30, the IR LED 96 and sensor 98 are mounted on opposite sides of the slotted skirt 92, with the IR LED 96 protruding through a hole 118 in the frame 4. Radiation emitted by the IR LED 96 is received at the sensor 98 via the slots 94 in the skirt 92. As the turn knob 76 is rotated, the interruptions in received IR radiation at the sensor generate a pulse which is conveyed to the processing unit 16, enabling the amount and direction of rotation to be determined. The incremental nature of the encoder formed by the IR LED 96 and sensor 98 results in an input device having no maximum or minimum position, merely registering an amount and direction of angular displacement of the turn knob 76.

The discrete input device 74 of the user input unit 12 comprises a push button 100 which is received within the central opening of the annular turn knob 76. The push button comprises a planar disc 102 and stem 104 which extends from a central point of a lower face of the disc 102. The stem 104 engages ribs 106 extending from the support ribs 24 of the frame 4. The stem 104 and ribs 106 form a snap fit connection 108 that maintains the push button 100 in the central opening of the turn knob 76. The ribs 106 receive the stem 104 directly above a receptor 110 mounted on the circuit board 38. Pushing the push button 100 forces the stem into contact with the receptor 110, sending a signal to the processing unit 18 and so registering a discrete input event. Once pressure is released from the push button 100, the push button is urged back to its original position by a compressible o-ring 112 which is seated on the annular shelf 90 of the turn knob 78 and engages a lower face of the disc 102 of the push button 100, The stem 104 and o-ring 112 are sized such that the push button 100 is slightly recessed with respect to the turn knob 76. An upper face of the disc 102 of the push button 100 may be suitable to receive branding or other printed or engraved material 114.

In one example (not shown), the frame 4 and upper housing unit 54 may be shaped such that the user input unit 12 is angled with respect to a reference plane defined by the frame 4. With the apparatus 2 in place on the limb of a patient, the angling of the user input unit 12 may direct the user input unit towards the head of the user, making the apparatus 2 more convenient to interact with when in position, particularly if the apparatus 2 is mounted on the leg of a patient.

The feedback unit 14 of the apparatus 2 comprises a bank of light sources. In the illustrated example the light sources comprise LEDs, mounted in a circular array immediately below the upper annular face 84 of the turn knob 76. This upper annular face is translucent, thus allowing light emitted by the LEDs to be seen by a user through the annular face of the turn knob 76. Translucency may be achieved through material choice, or by appropriate selection of material thickness, or by a combination of material choice and thickness. Each LED is received in an open segment 116 defined by the radially extending fins 28 and the inner circumference of the cylindrical support 22. The fins 28 serve to limit the area of illumination of the LEDs as perceived through the turn knob 78, and so to ensure the effect of illuminating each individual LED may be clearly distinguished by a user.

In the illustrated example, the circular array of LEDs comprises a continuous bank of bi-colour (green/blue) LEDs. The feedback unit 14 also comprises two single colour (red) LEDs mounted on a side of the apparatus 2 at positions 118 either side of the opening 62 for the mini USB port. Other arrangements and colour choices for the LEDs may be envisaged. Operation of the LEDs is controlled by the processing unit 16. The single colour (red) LEDs may be employed to provide user feedback concerning status of the apparatus 2. For example a first of the red LEDs may indicate battery status while a second red LED may indicate memory status. The bank of bi-colour LEDs may be used both to represent input received via the user input unit 12 and to feedback information processed by the processing unit. In another example (not shown), the feedback unit may further comprise a vibrating and or audible feedback element such as a buzzer. Precise operation of the feedback unit 14 is discussed below with reference to operation of the apparatus 2.

Suitable materials for some of the above described apparatus components include Polyamide (PA) for the push button 100 and turn knob 75, Thermoplastic Polyurethane (TPU) for the housing 52 and Polyoxymethylene (POM) for the frame 4.

In use, the apparatus 2 functions as a standalone monitoring device that enables user interaction without additional need for cooperating computing devices such as a laptop or Smartphone. The user may interact with the apparatus 2 using the input unit 12 and via the feedback unit 14. Functioning of the apparatus according to a typical user scenario is explained below, followed by a detailed discussion of the processing supporting this functionality.

The apparatus 2 may in one example scenario be used by a rehabilitation patient in cooperation with a medical practitioner such as a physiotherapist. The physiotherapist may first assess a patient and devise a course of exercises to be performed by the patient in their own home. These exercises may comprise a series of movements to be performed by the patient, for example forward, rearward and lateral leg raises for a patient recovering from hip replacement surgery. Each exercise may be defined by the linear and angular acceleration to be experienced by the leg during correct performance of the exercise. Values for the mean and standard deviation of the linear and angular acceleration corresponding to each exercise prescribed for the patient may be recorded in the memory of the apparatus 2. This is one example of how a pattern of motion corresponding to a single exercise may be digitally represented on the memory 18 of the apparatus 2. Other examples may be envisaged. Each exercise in the patient's prescribed program may be stored in the memory as its representative motion pattern together with the number of repetitions of the exercise to be conducted by the patient each day. Correct performance of the prescribed exercises, as well as operation of the apparatus 2 may be explained to the patient before the patient is sent home to conduct the program of exercises in their own home, away from the direct supervision of the physiotherapist.

When the patient is ready to conduct the exercises in their home, the patient first attaches the apparatus 2 to the appropriate limb using the strap 8. The strap 8 is passed around the limb of the patient, the two ends 36 of the strap 8 being passed through their respective openings 34 and folded back to fasten against the encircling portion of the strap 8, It is envisaged that Velcro® or a similar fastening mechanism may be used, allowing for considerable adjustment to accommodate different limb circumferences. Such a system offers the advantage of combining both attachment and adjustment of the strap in a single action. In the case of a patient requiring rehabilitation of a lower limb, the apparatus 2 offers the additional advantage that it may be attached to the lower limb with the patient in a sitting position, without requiring significant flexibility or dexterity on the part of the patient.

Once the apparatus 2 is comfortably attached to the limb, the patient commences the first exercise of their assigned program. As the patient moves their limb with the attached apparatus 2, the accelerometer and gyroscope of the motion sensing unit 10 sense the motion of the limb and the processing unit 16 calculates the mean and standard deviation and then compares the sensed motion pattern to the motion patterns stored in the memory 18. Suitable sampling rates, time intervals and measurement resolution may be selected for the accelerometer and gyroscope to facilitate exercise recognition. The k-nearest neighbour algorithm may also be used to assist with pattern recognition. If the processing unit 16 recognises the sensed motion pattern as resembling a stored motion pattern corresponding to an assigned exercise of the patient program, the processing unit 18 causes the array of feedback LEDs to glow an assigned colour (for example green). In some examples, the timing of the glow may be matched to the motion of an exercise. For example, if the exercise comprises lateral leg raises, the feedback LEDs may glow progressively as the leg is raised and fade as the leg is lowered. In this manner, the patient is reassured that they are conducting the exercise approximately correctly, as their motion is sufficiently close to the stored motion pattern for the exercise to have been recognised. If at any time this exercise recognition feedback stops, this indicates that the motion pattern no longer matches the stored pattern, and the patient is reminded to check that they are still conducting the exercise properly. If the apparatus 2 additionally comprises an audible feedback device such as a buzzer, this may be used to provide alternative or additional exercise recognition feedback, ensuring that the patient may receive this feedback even when the exercise results in the apparatus being out of view or difficultly visible by the patient (for example during rear leg raises). Each completed repetition of an exercise is stored in the memory 18 along with a time stamp and the degree of accuracy with which the exercise was conducted, i.e. the extent to which the sensed motion pattern matched the stored motion pattern. The threshold level for pattern similarity allowing exercise recognition may be adjusted to require a greater or lesser degree of accuracy in conducting an exercise before the exercise is recognised.

In some embodiments, the processing unit 16 may cause the number of LEDs providing exercise recognition feedback to represent the proportion of the allotted program of exercises so far completed. For example, if the program consists of a total of 20 repetitions, 10 repetitions of each of two different exercises, and the LED bank comprises 10 bi-colour feedback LEDs, the processing unit 16 may cause a single LED to glow providing exercise recognition feedback for the first two repetitions. For the third and fourth repetition, both the originally glowing LED and a neighbouring LED may be caused to glow in synchronisation with the completing of the exercises. The LEDs may be progressively illuminated as the repetitions are completed, showing the patient at a glance how far through the day's assigned program of exercises he or she has progressed. This progression feedback may also be requested by the patient during a pause in activity by pushing the push button 100. Depression of the push button 100 when an exercise is not taking place may be interpreted as a request for progression feedback, and the processing unit 16 may case an appropriate number of LEDs to glow their assigned colour (for example green) to demonstrate the proportion of the day's prescribed exercises that have been completed.

During completion of any exercise, the patient may provide feedback to the apparatus 2 via the input unit 12. This may be particularly advantageous in allowing the user to indicate a level of pain or discomfort experienced during completion of the exercise. The pain or discomfort experienced during particular exercises can provide valuable insight to the supervising physiotherapist as to the progress of the rehabilitation. By enabling the patient to provide that feedback during completion of the exercises, the apparatus contributes to gathering and storing relevant information on which the supervising physiotherapist may base further treatment.

A level of pain or discomfort may be input by the patient by turning the rotary knob 76 during or shortly after completion of an exercise. When turning of the rotary knob 76 is registered by the rotary encoder 78, the pulse generated by the encoder 78 is transmitted to the processing unit 16 which causes the bi-colour LEDs to illuminate in their second colour (for example blue) according to the amount of rotation detected. The more the rotary knob 76 is turned, the greater the number of illuminated LEDs, indicating a greater degree of pain. The LEDs are progressively illuminated in either a clockwise or anticlockwise direction, according to the direction in which the rotary knob is turned, thus allowing for both left and right handed patients. After an initial rotation in a first direction, causing illumination of an appropriate number of LEDs, should the rotary knob 76 be rotated back in an opposite direction to the initial rotation, the illuminated LEDs are progressively turned off. The patient may thus adjust the amount of rotation to indicate precisely the level of discomfort they are feeling from a minimum level of zero pain (no turning of the rotary knob 54 and hence no LEDs illuminated) to a maximum level of pain (all LEDs illuminated). Once the patient is satisfied that the proportion of LEDs lit accurately reflects his or her level of discomfort, the patient presses the push button 100 to register the pain input, at which point the pain level is saved in the memory 18 along with a time stamp, allowing the pain input to be matched to the exercise being conducted at the time the pain input was provided. The step of pressing the push button 100 to register pain feedback from the patient ensures that any accidental rotation of the knob is not mistaken for pain feedback, as well as allowing time for the patient to adjust the pain level to accurately reflect their experience before it is saved in the memory 18.

Once the patient has finished exercising they may remove the apparatus 2 until the next exercise session. In some examples, the apparatus 2 may incorporate a reminder function, causing the LEDs to glow on and off periodically even when no motion is sensed, so as to remind the patient that the exercise program for the current day has not yet been conducted. Pressing of the push button 100 during the reminder may "snooze" or cancel the reminder. If at any time the patient notices the battery feedback LED glowing red, the patient knows to place the apparatus 2 on charge for example via a suitable USB cable and charger. If the patient notices the memory LED glowing red, this suggests that at the next appointment with the physiotherapist, the patient data should be downloaded to a computer or other suitable device and deleted from the memory, to free up additional capacity. During data download, the battery may additionally be recharged using the computer or other device's power source. In view of the need for physiotherapist to download data from the apparatus memory, it is envisaged that the memory LED would start to indicate low memory well before the memory is actually exhausted.

During the patient's next appointment with the physiotherapist, the physiotherapist may download the data stored on the memory to a computer, allowing both the physiotherapist and the patient to study the data recorded in order to assess the patient's progress. A suitable computer platform may be developed to represent the data recorded on the apparatus to the physiotherapist and user, for example in graphic form. Examples of insights that may be gained by the physiotherapist thanks to the data collected by the apparatus 2 include:

To what extent the prescribed program of exercises was completed

With what degree of accuracy the prescribed exercises were completed

Which, if any, exercises caused particular discomfort

These insights may assist the physiotherapist in determining the effectiveness of the prescribed program and identifying any additional explanation or demonstration that may be needed as well as future modification of the program to accommodate the patient's progress. The input received from the patient concerning levels of pain or discomfort experienced enables the identification of problem movements and areas of difficulty, so enabling accurate targeting and evolution of the patient's future rehabilitation program.

Figure 9:
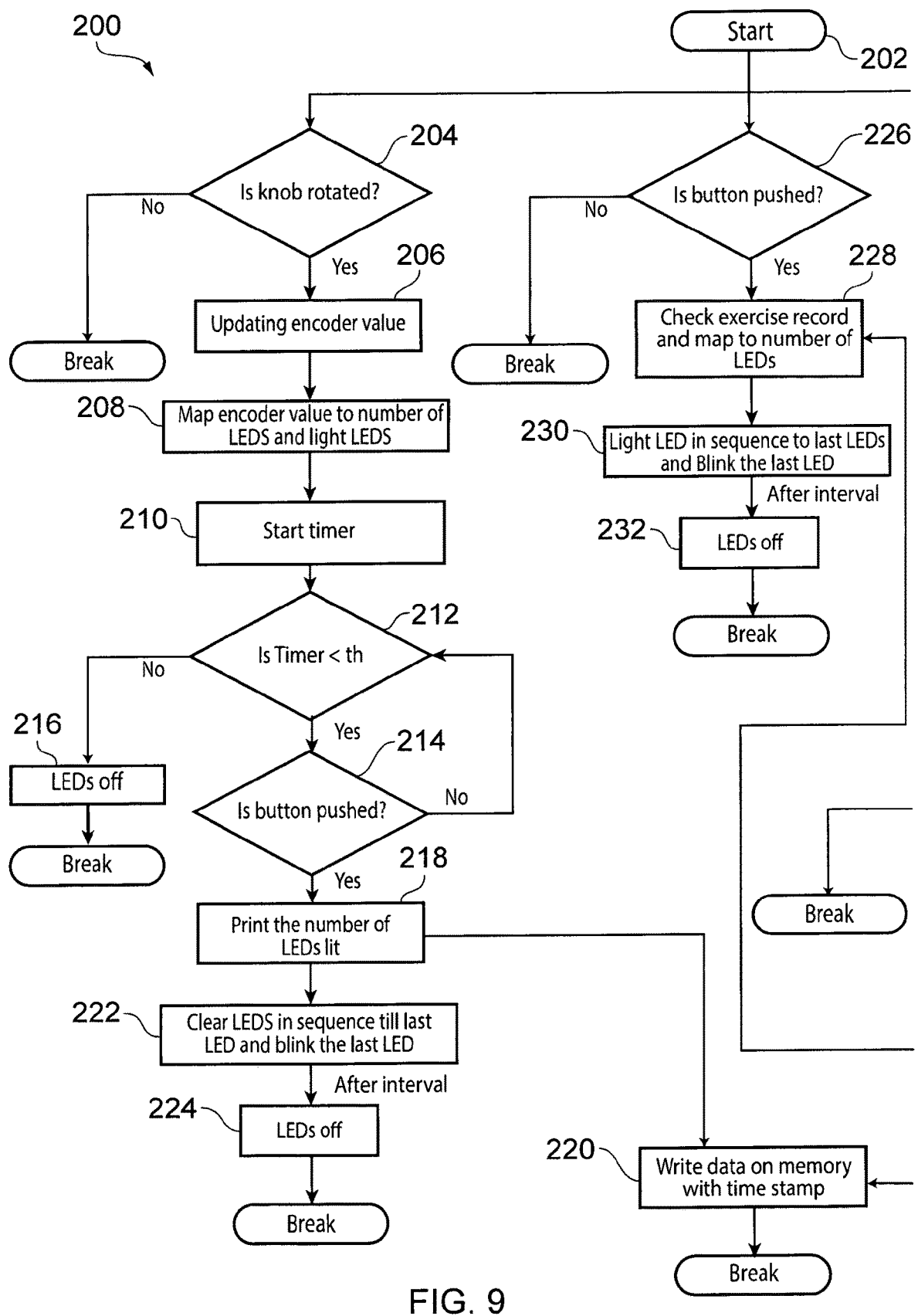
FIG. 9 is a chart illustrating an example of process flow for the apparatus of FIG. 1.
Figure 9:
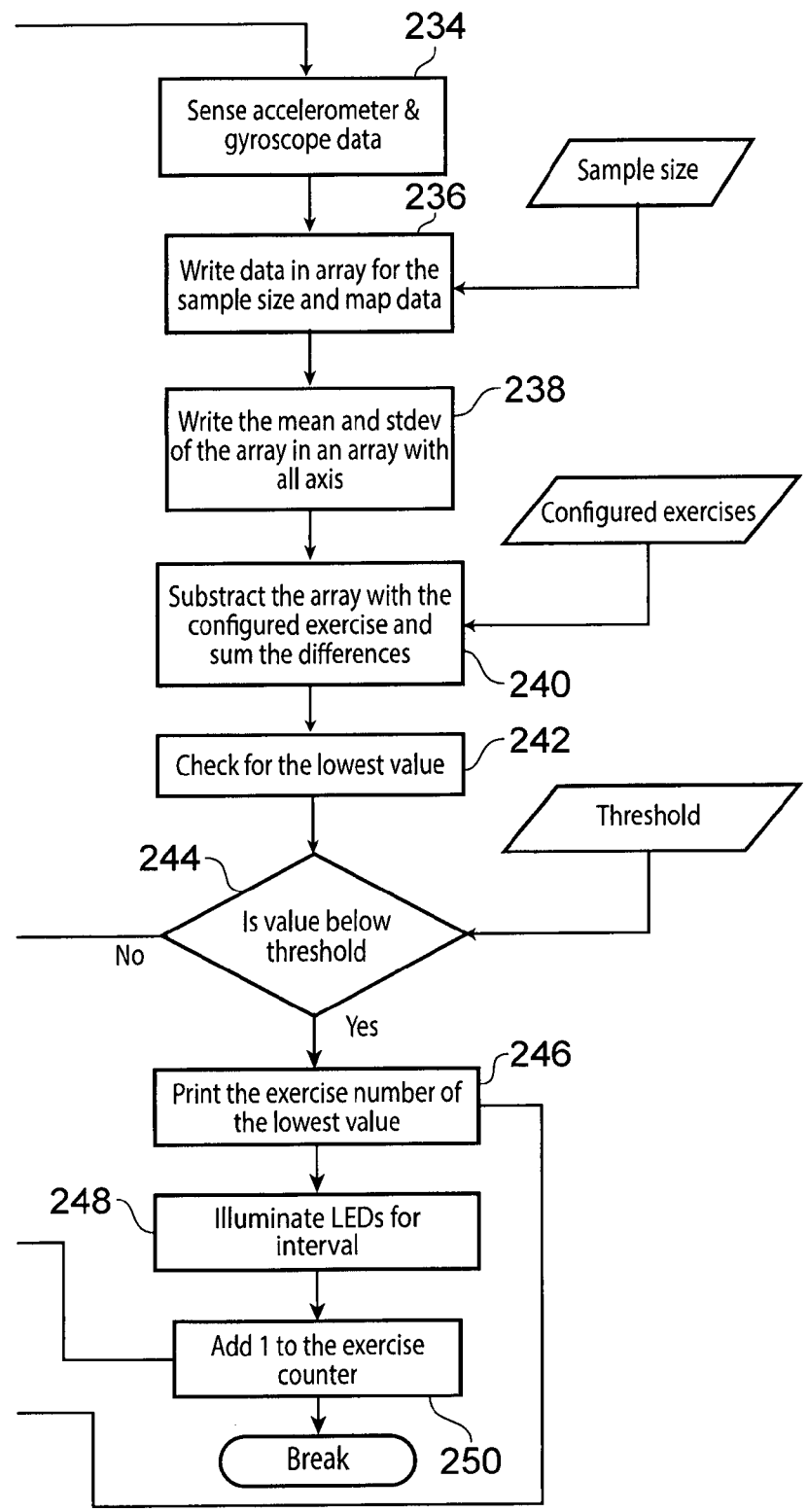

The apparatus functionality described above is achieved by appropriate interaction between the components of the apparatus 2, managed by the processing unit 16. An example of process flow for the processing unit 16 is illustrated in FIG. 9 and discussed in further detail below.

The process flow 200 starts at step 202 and follows three principle interlinked strands according to whether the turn knob 76 is rotated, the push button 100 is pressed and/or movement is sensed. At each break point in the process flow, the process returns to the start step 102. In a step 204, the processing unit 16 determines whether or not the turn knob 76 has been rotated. If the turn knob 76 has not been rotated, the process flow breaks. If the turn knob 78 has been rotated (Yes at step 204), the rotary encoder value is updated at step 206 and the updated encoder value is then mapped to the number of feedback LEDs, allowing the appropriate number of feedback LEDs to be illuminated in the appropriate colour (for example blue) in step 208. In this manner, the continuous input from the turn knob 76 is translated to discrete feedback elements (the illuminated LEDs) to give the user an easy to read representation of the input they have provided. The amount of turn knob rotation required for each new LED to be illuminated may be selected to facilitate maximum ease of use. For example, a single complete revolution of the turn knob 76 may equate to all of the feedback LEDs being illuminated, i.e. maximum pain level. For a bank of 10 LEDs, this equates to a rotation of 36 degrees per illuminated LED, and represents a balance between the motor control required in the user to manipulate the turn knob accurately and the speed with which the user may navigate from minimum to maximum pain input.

The LEDs are lit in sequence from a first LED until the appropriate number of LEDs is lit to represent the amount of rotation registered. The processing unit 16 then starts a timer in step 210 and checks for expiry of the timer in step 212. If the timer has not yet reached a threshold value (Yes in step 212) then the processing unit 16 checks for registering of depression of the push button 100 in step 214. While no pressing of the push button 100 has been registered, the processing unit 16 continues to check for expiry of the timer (No in step 214 and Yes in step 212). If the timer expires before the push button 100 is pressed (No in step 212) then the feedback LEDs are turned off in step 216 and the process flow breaks. If the push button 100 is pressed before the timer expires (Yes in step 214) then the user input is registered by printing the number of illuminated LEDs at step 218 and writing this data to the memory 18 in step 220 along with a time stamp of the time at which the push button 100 was pressed to register the user input. Following printing of the number of illuminated LEDs at step 218, the LEDs are turned off in sequence until the last LED (the first to be lit) is blinked for an interval of for example three seconds at step 222 before also being turned off at step 224. Having completed registering of the patient input, the process flow then breaks to return to the start.

From the start step 202, in a step 226, the processing unit 16 determines whether or not the push button 100 has been pressed. If the push button 100 has not been pressed (No in step 226), the process flow breaks. If the push button 100 has been pressed, the processing unit 18 checks the record of completed exercise repetitions for the day, compares this to the stored patient program in the memory and maps the proportion of the program which has been completed to the number of feedback LEDs in step 228. The processing unit then lights the mapped number of feedback LEDs in sequence at step 230 and blinks the last LED to be lit for a time interval of for example 3 seconds, indicating to the user the proportion of exercise repetitions completed for the present day. After the time interval has expired, all LEDs are switched off at step 232 and the process flow breaks to return to the start.

From the start step 202, in a step 234 the accelerometer and gyroscope of the motion sensing unit 10 sense motion of the apparatus 2. The processing unit 16 then conducts exercise recognition in steps 236 to 244. In step 236 the sensed data is written into an array appropriate to the sample size selected for the accelerometer and gyroscope. In step 238, the mean and standard deviation for each axis are calculated and these are then compared to the motion patterns of the stored exercises in the memory 18 at step 240. The comparison is conducted by subtracting the mean and standard deviations of the sensed data from the mean and standard deviation values for the motion patterns of each of the stored exercises. Each exercise comparison produces a results value and the lowest of these values is selected in step 242. Owing to the subtraction calculation, the lowest results value represents the stored exercise which most closely resembles the sensed motion pattern, in step 244 this lowest value is compared to a threshold value representing exercise recognition. If the value is not below the threshold (No at step 244) then the sensed exercise pattern is not sufficiently similar to any of the stored exercise patterns to be recognised as one of the stored exercises. The process flow then breaks and returns to the start at step 202. If the lowest value is below the threshold value (Yes at step 244) then the sensed exercise has been recognised as the stored exercise corresponding to the lowest comparison value. The exercise number of this exercise is printed in step 246 and the feedback LEDs are temporarily illuminated an appropriate colour (for example green) in step 248. The counter for the recognised exercise is then increased by 1 in step 250 before the process flow breaks and returns to the start. It will be appreciated that the exercise counter that is updated at step 250 is used in step 228 to assemble the total number of completed exercises for the day and compare this to the stored patient program.

The flow chart of FIG. 9 illustrates an example in which progress feedback is given after each exercise repetition. After a recognised exercise has been completed for a single repetition, and the exercise counter has been increased by one at step 250, the processing unit proceeds to steps 228, 230 and 232 in which the daily progress through the stored program is calculated and represented to the user through illumination of the appropriate proportion of feedback LEDs. In other examples, (not illustrated), progress feedback and exercise recognition may be combined by lighting the appropriate number of LEDs to give progress feedback during the exercise recognition feedback step 248, Alternatively, the two feedback elements may be completely separate, with all LEDs glowing for exercise recognition and progress feedback only being given on request via pushing of the push button 100.

Additional variations to the process flow illustrated in FIG. 9 may be envisaged. For example, while checking for pushing of the button in step 214, the processing unit may also check for further rotation of the turn knob 78, in either the initial or reverse directions. Such rotation, if detected, may be reflected in the number of LEDs illuminated and may cause a restarting of the timer of step 210. Additionally, should the timer of step 210 expire before the push button 100 is pressed, the number of LEDs illuminated at the time of expiry may be stored in a temporary memory. As soon as further rotation is sensed, the last saved LED configuration may be retrieved such that the same number of LEDs are immediately illuminated, returning the user to their last input situation. Once input is registered by pressing of the push button 100, the temporary memory may be cleared. In this manner, should a user take longer that the threshold delay to decide whether the illustrated pain level is representative before pushing the push button 100, they may recommence immediately simply by making an additional rotational motion of the knob 76.

A reminder function may also be incorporated into the process flow of FIG. 9, For example, at specified times of day the feedback LEDs may be programmed to glow if no exercises have yet been sensed by the apparatus 2 during the day. During display of the reminder, pressing the push button 100 may have the effect of "snoozing" or cancelling the reminder.

Another variation to the process flow and functionality which may be considered includes the addition of a further LED within the push button 100. According to one example, this push button LED may be caused to glow as soon as rotation of the knob 78 is registered, so prompting the user to push the push button 100 and so register the pain input information.

The three principle strands of process flow shown in FIG. 9 (following rotation of the turn knob 78, pushing of the push button 100 or sensed motion) are illustrated as running substantially in parallel A hierarchy may be imposed to address potential conflict between the strands, should multiple actions taking place contemporaneously cause conflicting instructions for example regarding the number of LEDs to be illuminated. In one example, the hierarchy may place user input of maximum importance, such that illuminating LEDs to reflect rotation of the turn knob 76 (pain input) will always be given priority over illuminating the LEDs for any other reason, for example to provide progress feedback. Alternative priorities for LED illumination may be envisaged for particular use cases.

FIGS. 10*a* to 10*f* illustrate feedback states of the array of LEDs forming the feedback unit 14. In the illustrated arrangement, the array comprises 10 bi-colour (green/blue) feedback LEDs, 1 red battery LED and 1 red memory LED. The bi-colour LEDs are illuminated green for progress feedback and exercise recognition, and blue to represent pain input. The array is illustrated as a single linear array for ease of representation. However it will be appreciated that in the examples of FIGS. 1 to 7, the bi-colour LEDs are arranged in a circular array, with LED1 adjacent to LED10, and the red battery and memory LEDs are mounted on a side of the apparatus 2, Each of FIGS. 10*a* to 10*f* illustrates illumination of the various LEDs against time for different feedback situations.

Figure 10A:
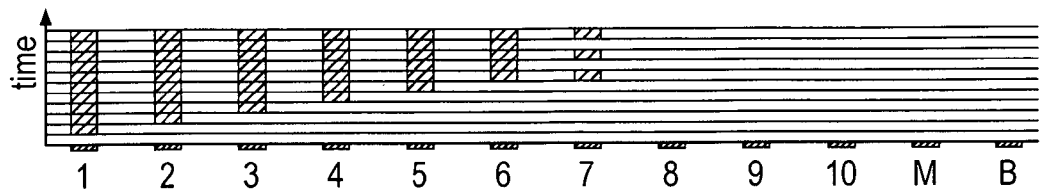
FIGS. 10a to 10f are graphs representing illumination patterns for the apparatus of FIG. 1.

FIG. 10*a* represents progress feedback, prompted by pressing of the push button 100 without turning of the turn knob 76. In the illustrated case, the proportion of the assigned program of exercises that have been completed maps to 6 out of the 10 LEDs being illuminated green. LED1 is illuminated first, followed by LED2, LED3, etc until LED 7 is caused to flash, signalling that the user has completed 80% of the exercises and is currently working towards 70% of the program.

Figure 10B:
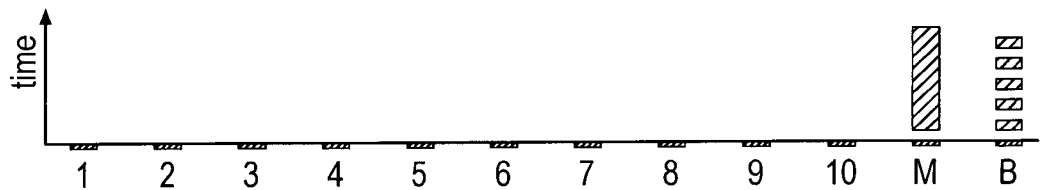

FIG. 10*b* illustrates battery and memory feedback. The memory LED is glowing solid red, indicating that the available memory space is approaching low values and the stored data should be cleared at the next opportunity. When the available memory reaches a critical level, the memory LED will blink red. The battery LED is blinking red, indicating that the battery is low and should be charged. A solid glowing battery LED would indicate that the battery is approaching low status while the blinking LED indicates the battery has reached low levels and should be charged.

Figure 10C:
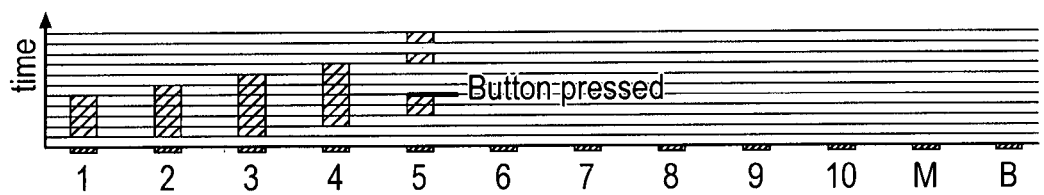

FIG. 10*c* illustrates pain input from a user. The user has turned the turn knob 76 by an amount corresponding to 5 of the 10 LEDs being illuminated (blue). The user then pushes the push button 100 to register the pain input, at which point the LEDs sequentially turned off, starting with LED1 until only the last illuminated LED (LED5) remains. This last LED begins to blink, indicating successful registration of the pain input before also being turned off.

Figure 10D:

FIG. 10*d* illustrates exercise recognition. On recognising completion of a stored exercise, the processor causes all of the bi-colour LEDs to blink (green) together, indicating that the current exercise has been recognised. As discussed above, the feedback situations of FIGS. 10*a* (progress feedback) and 10*d* (exercise recognition) may be combined by causing only the number of LEDs corresponding to the proportion of the assigned program which has been completed to blink on recognising completion of the stored exercise. Thus in the example of FIGS. 10*a* and 10*d*, the first 6 LEDs would blink on recognition of the exercise. Once enough additional exercise repetitions have been completed to represent completion of 70% of the assigned program, 7 out of the 10 LEDs would blink to single exercise recognition, and so on.

Figure 10E:

FIG. 10*e* illustrates the reminder function, with all bi-colour LEDs blinking alternately blue and green while no movement is taking place, reminding the user to perform their exercises.

Figure 10F:

FIG. 10*f* illustrates synchronisation with a computer, during which data may be uploaded to and downloaded from the apparatus 2. During this time the bi-colour LEDs may be each individually illuminated in sequence.

The apparatus 2 thus represents a self-contained monitoring unit with which a user may interact both to receive feedback and to provide input. The continuous input 25 device enables the capture of relatively detailed information concerning user pain in a manner that is easy to master for users of all ages and abilities. The combination of discrete and continuous user input devices further facilitates the capture and display of information useful both to a user and to a medical practitioner such as a physiotherapist.

The invention claimed is:

1. An apparatus for user exercise monitoring, comprising:
  a frame;
  a motion sensing unit, a processing unit, a memory, a feedback unit, and a user input unit supported by the frame; and
  a harness configured to secure the frame to a user body part;
  wherein the user input unit comprises a continuous input device and a discrete input device, the continuous input device comprising a rotary device including a turn knob and cooperating rotary displacement measurement element, the rotary displacement measurement element comprising a rotary encoder operable to transmit a signal to the processing unit representative of an amount of rotation detected, the discrete input device defining a center portion of the turn knob and operable such that depression of the turn knob transmits a signal to the processing unit to register a discrete input event;
  wherein the memory includes a plurality of post-surgical rehabilitation exercises stored therein, each of the exercises defined by a stored motion pattern;
  wherein the processing unit is configured to receive data from the motion sensing unit such that, in use, the processing unit is operable to identify completion of the exercises by comparing the data with the stored motion patterns;
  wherein the feedback unit is configured to receive instructions from the processing unit to display reminders at specified, programmed times during a day if none of the exercises have been sensed by the motion sensing unit during the day; and
  wherein the user input device is configured such that depression of the turn knob during display of the reminders has the effect of snoozing the reminders for a prescribed time period.

2. The apparatus as claimed in claim 1, wherein the motion sensing unit comprises at least one of an accelerometer and a gyroscope.

3. The apparatus as claimed in claim 1, wherein the feedback unit comprises a plurality of light sources, and wherein the light sources are programmed to glow on and off periodically during the day to provide the reminders.

4. The apparatus as claimed in claim 1, wherein the feedback unit is configured to represent input from the input unit.

5. The apparatus as claimed in claim 1, wherein the processing unit is further configured to store a record of completed exercises in the memory.

6. The apparatus as claimed in claim 1, wherein the feedback unit is further configured to display feedback from the processing unit.

7. The apparatus as claimed in claim 1, wherein the post-surgical rehabilitation exercises comprise forward, rearward, and lateral leg raises.

8. The apparatus as claimed in claim 7, wherein each exercise is defined by an expected linear acceleration and an expected angular acceleration of a leg during correct performance of the exercise.

9. An apparatus for user exercise monitoring, comprising:
  a frame;
  a motion sensing unit, a processing unit, a memory, a feedback unit, and a user input unit supported by the frame; and
  a harness configured to secure the frame to a user body part;
  wherein the user input unit comprises an input device operable to receive continuous input through rotational movement of the input device and discrete input through translational movement of the input device, the input device comprising a turn knob rotatable relative to the frame about a knob center axis and a cooperating rotary displacement measurement element, the turn knob depressible toward the frame along the knob center axis;

wherein one or more exercises are stored in the memory, each of the one or more exercises comprising a plurality of exercise repetitions;

wherein the processing unit is configured to receive data from the motion sensing unit and identify completion of each exercise repetition based on a comparison with motion patterns stored in the memory;

wherein a repetition time stamp associated with the completion of each exercise repetition is stored in the memory;

wherein the input device is operable to receive user input corresponding to a level of pain or discomfort experienced by the user during completion of each exercise repetition;

wherein the level of pain or discomfort is stored in the memory, along with a pain time stamp, to match the level of pain or discomfort to the exercise repetition being performed at the time the user input was provided; and wherein the feedback unit is configured to display feedback from the processing unit, the feedback unit comprising a light source operable to provide visual feedback, a vibration element operable to provide haptic feedback, and an audio element operable to provide audible feedback.

10. The apparatus as claimed in claim 9, wherein the processing unit is configured to store a record of completed exercises in the memory.

11. The apparatus as claimed in claim 9, wherein the light source comprises a plurality of feedback light-emitting diodes (LEDs).

12. The apparatus as claimed in claim 11, wherein the feedback LEDs are arranged in a circular array.

13. An apparatus for user exercise monitoring, comprising:
- a frame;
- a motion sensing unit, a processing unit, a memory, a feedback unit, and a user input unit supported by the frame; and
- a harness configured to secure the frame to a user body part;

wherein the user input unit comprises a continuous input device and a discrete input device, the continuous input device comprising a rotary device including a turn knob and cooperating rotary displacement measurement element, the rotary displacement measurement element comprising a rotary encoder operable to transmit a signal to the processing unit representative of an amount of rotation detected, the discrete input device defining a center portion of the turn knob and operable such that depression of the turn knob transmits a signal to the processing unit to register a discrete input event;

wherein the memory includes a program of post-surgical rehabilitation exercises stored therein, each of the exercises defined by a stored motion pattern;

wherein the processing unit is configured to receive data from the motion sensing unit such that, in use, the processing unit is operable to identify completion of the exercises by comparing the data with the stored motion patterns and to store a record of completed exercises in the memory;

wherein the feedback unit is operable to provide feedback to the user indicating a proportion of the program completed by the user and a degree of accuracy in which each of the exercises was completed by the user;

wherein the degree of accuracy is based on a threshold level for pattern similarity stored in the memory; and wherein the threshold level is adjustable to require a greater or lesser degree of accuracy.

14. The apparatus of claim 13, wherein the feedback unit comprises a light source operable to provide visual feedback.

15. The apparatus of claim 14, wherein the feedback unit further comprises a vibration element operable to provide haptic feedback.

16. The apparatus of claim 14, wherein the light source comprises a plurality of feedback light-emitting diodes (LEDs).

17. The apparatus claim 16, wherein the feedback LEDs are arranged in a circular array.

* * * * *